United States Patent
Kodali et al.

(10) Patent No.: US 11,442,067 B2
(45) Date of Patent: Sep. 13, 2022

(54) PEPTIDE MAPPING METHOD FOR SEQUENCE IDENTIFICATION OF INSULIN AND INSULIN ANALOGUES

(71) Applicant: BIOCON LIMITED, Bangalore (IN)

(72) Inventors: Phanichand Kodali, Hyderabad (IN); Krishnappa Mane, Karnataka (IN); Srivatsa Koduru, Krishna District (IN); Ashutosh Sudhir Naik, Hyderabad (IN); Laxmi Adhikary, Bangalore (IN)

(73) Assignee: BIOCON LIMITED

( * ) Notice: Subject to any disclaimer, the term of this patent is extended or adjusted under 35 U.S.C. 154(b) by 426 days.

(21) Appl. No.: 16/633,404

(22) PCT Filed: Jul. 20, 2018

(86) PCT No.: PCT/IB2018/055420
§ 371 (c)(1),
(2) Date: Jan. 23, 2020

(87) PCT Pub. No.: WO2019/021133
PCT Pub. Date: Jan. 31, 2019

(65) Prior Publication Data
US 2020/0378984 A1    Dec. 3, 2020

(30) Foreign Application Priority Data
Jul. 25, 2017 (IN) .............................. 201741026454

(51) Int. Cl.
*G01N 33/68* (2006.01)
*G01N 30/02* (2006.01)
*G01N 30/72* (2006.01)

(52) U.S. Cl.
CPC ......... *G01N 33/6848* (2013.01); *G01N 30/02* (2013.01); *G01N 30/7233* (2013.01);
(Continued)

(58) Field of Classification Search
CPC .......... G01N 33/6848; G01N 33/6818; G01N 33/68; G01N 30/02; G01N 30/7233;
(Continued)

(56) References Cited

U.S. PATENT DOCUMENTS 7,622,273 B2  11/2009 Gibbs
9,581,601 B2  2/2017 Cindric et al.
(Continued)

FOREIGN PATENT DOCUMENTS

CN          105301125        2/2016

OTHER PUBLICATIONS

Hsu, Jia-Chaun et al. Identification of Recombinant Insulin Analogues by Peptide Mapping Method, *Journal of Food and Drug Analysis*, 2012, 20(4):957-962.
(Continued)

*Primary Examiner* — Kiet T Nguyen
(74) *Attorney, Agent, or Firm* — Marianne Fuierer; Casimir Jones, S.C.

(57) ABSTRACT

The invention relates to peptide mass fingerprinting technique for the proteins such as Human insulin and insulin analogs. The insulin analogues can vary at least by one amino acid, which is elusive to distinguish by currently available analytical methods. The invention further allows sequence confirmation of the peptide wherein the run time of the method is forty minutes. This method could be applied for molecules up to 50 kDa.

8 Claims, 16 Drawing Sheets

Specification includes a Sequence Listing.

(52) U.S. Cl.
CPC ......... *G01N 33/68* (2013.01); *G01N 33/6818* (2013.01); *G01N 2333/62* (2013.01); *G01N 2560/00* (2013.01)

(58) Field of Classification Search
CPC ..... G01N 2333/62; G01N 2333/96441; G01N 2560/00; G01N 2800/042
USPC ........................................................ 250/282
See application file for complete search history.

(56) References Cited

U.S. PATENT DOCUMENTS

| | | | |
|---|---|---|---|
| 2003/0028920 A1* | 2/2003 | Altier ................. | C12N 15/8282 435/6.16 |
| 2008/0044854 A1* | 2/2008 | Wang ....................... | C12N 9/93 435/243 |
| 2009/0093405 A1* | 4/2009 | Wallen, III ........ | A61K 39/0005 530/399 |
| 2012/0100071 A1 | 4/2012 | Valliant et al. | |

OTHER PUBLICATIONS

Moller, Charlotte et al. Determination of the binding sites for oxaliplatin on insulin using mass spectrometry-based approaches, *Anal Bioanal Chem*, 2011, 401:1619-16-29.

Hoober JK et al, Structural similarities between the major polypeptides of thylakoid membranes from Chlamydomonas reinhardtii, Arch Biochem Biophysics, 202 (1) 1980, 221-234.

* cited by examiner

PEPTIDE MAPPING METHOD FOR SEQUENCE IDENTIFICATION OF INSULIN AND INSULIN ANALOGUES

CROSS-REFERENCE TO RELATED APPLICATIONS

This application is filed under the provisions of 35 U.S.C. § 371 and claims the priority of International Patent Application No. PCT/IB2018/055420 filed on Jul. 20, 2018 which in turn claims priority to Indian Patent Application No. 201741026454 filed on Jul. 25, 2017, the contents of which is hereby incorporated by reference herein for all purposes.

FIELD OF INVENTION

The present invention relates to the field of proteomics and analytical chemistry. More particularly, the invention relates to method of development of peptide mass fingerprint for the proteins for simultaneous determination of identity and masses which further allows sequence confirmation of the peptide.

BACKGROUND OF INVENTION

Methods using gel electrophoresis and mass spectrometry, which employ sensitive instruments, are known for the rapid quantitative analysis of proteins. These methods include extracting the protein, digesting at least a portion of proteins and making sample, electrophoresing, detecting the difference in the expression levels of the proteins in samples by mass spectrometry based on peptides in the sample of labelled peptides. This analytical method can be used for qualitative and quantitative analysis of protein expression profiles. However, the method includes many chemicals and several steps that adds to its huge cost. Thus, there is a need to develop a method that reduce the cost and time.

Proteins obtained by recombinant DNA technology are identified by peptide mapping method. Peptide mapping is an influential test capable of identifying single amino acid changes resulting from events such as errors in point mutations. Peptide mapping method can be used to evaluate the stability of the expression construct of cells used for recombinant DNA products and to assess product stability, as well as to ensure the identity of the protein product, or to detect the presence of protein variants. Peptide mapping is also used to evaluate the quality of commercial insulin products and to set up a peptide mapping method suitable for screening proteins such as human insulin and insulin analogues.

U.S. Pat. No. 7,622,273 describes the step by step method in which proteins directly bind to protein microarrays (protein chip), and chemical treatment/enzymatic digestion/chemical digestion follows. Digestion by chemical treatment step includes protein denaturation, reduction and alkylation. Enzymatic digestion step includes de-glycosylated proteins or dephosphorylated and enzymatic hydrolysis or chemical proteolysis of the protein. All reactions on protein microarrays are performed step by step for rapid protein identification and structural characterization. Although this method takes less duration than the conventional method, which consume about 24 hours, it is still unsatisfactory. More importantly, the complex samples (plasma, urine, cerebrospinal fluid, etc.) may require fractionation before implementing this method to obtain target protein isolate, which therefore increases the overall processing and duration. Hence, it leads to extra cost and time required for sample preparation and expected results.

U.S. Pat. No. 9,581,601 describes a method of derivatization of peptides/proteins by compounds comprising two or more sulfonyl groups and analysis of derivatized analytes in negative mode of operation of mass spectrometer. This method allows analysis of amino acid sequence of long-chain peptides/proteins. It also relates to synthesis procedure of 5-formyl-benzene-1,3-disulphonic acid as derivatization compound. Derivatization of a new reagent is time consuming and has additional costs associated with it.

The conventional desalting permits the detection of only individual fragments at a time and requires multiple chromatographic runs followed by desalting of collected individual peaks. The method takes up to two working days.

The peptide mapping procedures for insulin and its analogues so far available in the literature are pertaining to salt-based methods, which are not compatible for the LC-MS usage. Thus, there was a need to develop a new peptide mapping fingerprinting method which has a shorter run time and is LC-MS compatible. Since the insulin analogues vary by 1 to 3 amino acids, it is difficult to perform protein mapping, especially of such peptides in a time efficient manner.

Thus, there remains a need for a method which not only reduces the time and cost incurred but also provides reliable results.

OBJECT OF INVENTION

Accordingly, an object of the present invention is to provide a time and cost effective method of peptide mapping fingerprinting for determination of identity and masses of the protein/peptides.

Another object of the present invention is to provide a method wherein the protein is dissolved in a non-salt buffer that results in the drastic reduction in the run-time in comparison to conventional methods.

Another object of the present invention is to provide a method wherein it also allows the detection of multiple fragments at the same time.

Another object of the present invention is to provide the sequence confirmation by eliminating desalting step and reduce the time required to analyse the sample.

SUMMARY OF INVENTION

An aspect of the present invention is a method for determining the amino acid sequence and mass of polypeptide(s) such as insulin or insulin analogs (aspart, lispro or glargine) ranging from 0.4 kDa to 8 kDa, wherein polypeptide differ by at least one amino acid, in reduced conditions, comprising the steps of: digestion of the polypeptide sample by addition of endoproteinase Glu C, reduction of digested sample; performing HPLC analysis followed by mass spectrometry analysis and comparing the molecular mass of the polypeptide with the molecular mass of a corresponding known polypeptide. The invention allows determination of identity of polypeptide and sequence confirmation of the peptide wherein the run time of the method of present invention is around forty minutes.

DESCRIPTION OF INVENTION

Definitions

Figure 1:
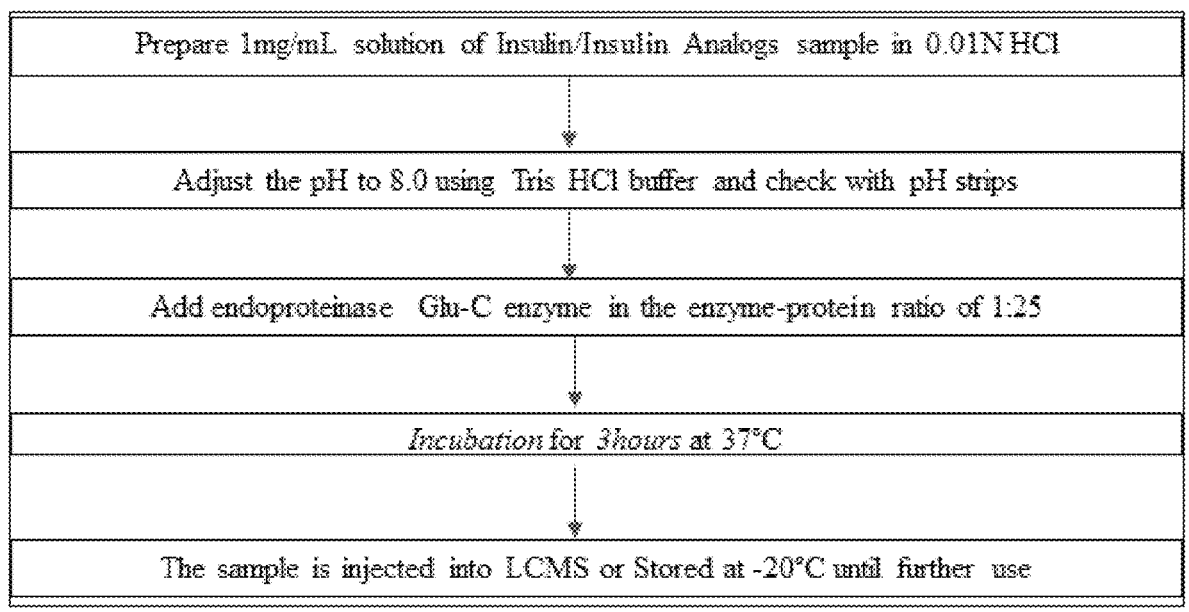
FIG. 1 represents flowchart of enzymatic digestion of working standards (in-house) and commercial products.

The term "polypeptide, "peptide" refer both to peptides and to polypeptides, naturally occurring or recombinant, produced or modified chemically or by other means, which may assume the three dimensional structure of proteins that may be post-translationally processed, essentially the same way as native proteins.

The term "peptide map" refers to a set of polypeptides that is obtained by fragmentation of a given polypeptide and, thus, specific for said polypeptide.

The term "protein sample" refers to in-house working standards and commercial products of insulin and insulin analogues viz. Insulin Aspart (Novolog), Insulin Lispro (Humalog), Insulin Glargine (Lantus).

The term "digestion" refers to cleavage of peptide by Endoproteinase GluC which cleaves at aspartic acid residues.

The term "reduction" refers to reduce the disulfide bonds of proteins, to prevent intramolecular and intermolecular disulfide bonds from forming between cysteine residues of proteins.

The term Insulin refer to a hormone which is 51 amino acid residue polypeptide (5808 Daltons), which plays an important role in many key cellular processes. It is involved in the stimulation of cell growth and differentiation. It also exerts its regulatory function (e.g. uptake of glucose into cells) through a signalling pathway initiated by binding of hormone in its monomeric form to its dimeric, tyrosine-kinase type membrane receptor. The mature form of human insulin consists of 51 amino acids arranged into an A-chain (GlyA1-AsnA21) and a B-chain (PheB1-ThrB30) of total molecular mass of 5808 Da. The molecule is stabilised by two inter-(A20-B19, A7-B7) and one intra chain disulphide bonds (A6-A11).

Insulin Analogue "Lispro" is identical in primary structure to insulin human, differs from insulin by switching the lysine at position B28 and the proline at position B29. It is a short-acting insulin monomeric analogue. In the solution formulation, lispro exists as an inherently destabilized hexamer, but when injected, it spontaneously dissociates into a monomeric form. The modification of the B chain C-terminus decreases the non-polar contacts and b-sheet interactions between insulin monomers, resulting in less self-association.

Insulin Analogue "Aspart" acts similarly to lispro. The rapid-acting analog aspart differs from human insulin by a single substitution of aspartic acid for proline at position B28. This substitution results in charge repulsion between monomers and steric hindrance due to a local conformation change at the carboxyl terminus of the B chain, reducing the formation of both hexamers and dimers, and thereby increasing the rate of absorption of monomeric aspart insulin.

Insulin Analogue "Glargine" differs from human insulin by a substitution of asparagine for glycine at A21, and the addition of two arginine residues to the C-terminus of the B-chain. Insulin glargine solution is formulated and injected at pH 4.0. These modifications increase the isoelectric point to a more neutral pH, reducing the solubility under physiologic conditions and causing glargine to precipitate at the injection site, thus slowing absorption. Glargine is an extended-action analogue that lasts 20-24 hour like ultralente insulin and reduces nocturnal hypoglycaemia in Type 1 and Type 2 diabetes patients better than neutral protamine Hagedorn (NPH) insulin.

Detailed Description of Invention

The present invention provides a method for determining the amino acid sequence and mass of a polypeptide or a mixture of polypeptide(s) comprising the steps of:
a) preparing polypeptide sample by dissolving the polypeptide in a strong acid HCl and pH adjusted by Tris;
b) digesting the polypeptide sample of step (a) by addition of endoproteinase Glu C in an enzyme-protein ratio of 1:25;
c) reducing the digested polypeptide of step (b) by addition of 1 M dithiothreitol.
d) performing HPLC analysis followed by mass spectrometry analysis of the polypeptide of step (c) involving an organic solvent;
e) comparing the molecular mass of the digested polypeptide with the molecular mass of a corresponding a known polypeptide, thereby determining the identity of the polypeptide, wherein the organic solvent is a non-salt buffer; and the method allows sequence confirmation of multiple fragments at the same time.

The non-salt buffer can be selected from a group consisting of acetonitrile, formic acid, TFA, or combinations thereof.

In conventional methods, salt based buffer used for LC-MS detection, however, the present inventors found that on use of non-salt based buffer compatible to LCMS leads to a significant reduction in the time consumed for step (d) and (e) thus making the present process time and cost efficient.

It was surprising found that the steps (d) and (e), that is after the step of digestion and reduction to identify masses and sequences, takes about 40 minutes while the conventional method takes one to two days.

The present method can be applied to analyse and identify mass and sequences of poly peptides up to 50 kDa.

Digestion of a peptide or protein can improve mass spectrometric detection as a result of increased charging and exposure of ionisable groups. In the present invention, reduction of protein involves cleaving the disulphide bridges in a peptide or protein. It is followed by the addition of alkylating agent to reduce and prevent the reformation of the disulphide bonds, which can lead to disulphide bond scrambling thus promoting amorphous aggregates.

I. Enzymatic Digestion of protein by Endoproteinase Glu-C in the ratio of 25:1 (protein to enzyme).
II. Enzymatic Digestion and reduction by adding 1 M DTT after digestion procedure with Endoproteinase Glu-C in the ratio 25:1 (protein to enzyme).
III. Analysis using a LC-MS (ESI) for the HPLC.
IV. Analysis using Protein mass fingerprinting (PMF) profiles.
V. Detection of multiple fragments and sequence confirmation of the peptide.
VI. Post the stage of digestion, the time of present invention is up to 40-60 mins.

As described in examples, following material and reagents were used in present invention.

1. 0.01 N HCl was used to prepare protein/peptide sample while Tris-HCl buffer was used to adjust the pH.
2. In the examples presented, the organic solvent, which is a non-salt based buffer, used was acetonitrile (ACN) from J. T Baker containing 0.1% formic acid (FA) of spectrophotometric grade (acquired from Sigma-Aldrich), though other organic solvents such as methanol (MeOH), isopropanol (IPA), or mixtures of ACN, MeOH and IPA could also be used.
3. In the examples presented, the solution comprises the reducing agent comprises a dithiol reducing agent 1M dithiothreitol (DTT). However, tris(2-carboxyethyl) phosphine (TCEP), 2-mercaptoethanol (BME), and 2-mercaptoethanolamine (2-MEA) could also be used.
4. Endoproteinase Glu-C (1 mg/ml) Sequencing grade (Roche, Cat #11047817001) used to prepare fragments of in-house as well as commercial products.
5. As presented in examples in-house working standards of Human Insulin, Insulin Glargine, Insulin Aspart and Insulin Lispro while commercial products—Novolin-R (Insulin by Novo-Nordisk), Lantus (Insulin Glargine made by Aventis), Novolog (Insulin Aspart made by Novo-Nordisk) and Humalog (Insulin Lispro made by Eli-Lilly) were used.

Two individual experiments were conducted in present invention. In first experiment protein/peptide sample of insulin and insulin analogs were treated only for digestion. In second experiment the protein/peptide sample of insulin and insulin analogs were treated for digestion as well as reduction.

Both the samples were analysed by using LC-MS (ESI) for the HPLC and by using Protein mass fingerprinting (PMF) profiles.

The description further describes the best mode of the procedure.

Step 1 Enzymatic Digestion of In-House Working Standards and Commercial Products Step by step procedure was followed as displayed in FIG. 1, wherein, the protein sample (1 mg/mL) was dissolved in 0.01 N HCl and the pH is adjusted to 7.5-8.5 with Tris-HCl buffer. Endoproteinase Glu-C was added in the ratio 25:1 (protein to enzyme). The sample was incubated at 37° C. for 3 hours, then the final sample was analysed using a LC-MS (ESI) for the HPLC and Protein mass fingerprinting (PMF) profiles. The sample was also stored at −20° C. for future use.

Peptide fragments obtained after digestion for Insulin molecule are listed in Table 1. Four peptide fragments were generated from insulin human after protease V8 digestion and were labelled as Fragment I, II, III, and IV.

TABLE 1

Tabulation of the theoretical Glu C digested peptide fragments of Insulin

| Analog | Sr. No. | Frag. No. | No. of AA | Position of Sequence | Sequence | | RRT |
|---|---|---|---|---|---|---|---|
| Human Insulin | 1 | I | 4 | [A(1-4)] | GIVE | SEQ ID NO: 1 | 0.38 |
| | 2 | II | 9 | [B(22-30)] | RGFFYTPKT | SEQ ID NO: 2 | 0.62 |
| | 3 | III | 12 | [B(14-21)]---[A(18-21)] | ALYLVCGE---NYCN | SEQ ID NO: 3 | 0.75 |
| | 4 | IV | 26 | [B(1-13)]---[A(5-17)] | FVNQHLCGSHLVE---QCCTSICSLYQLE | SEQ ID NO: 4 | 1 |
| Insulin Glargine | 1 | I | 4 | [A(1-4)] | GIVE | SEQ ID NO: 1 | 0.39 |
| | 2 | II | 11 | [B(22-32)] | RGFFYTPKTRR | SEQ ID NO: 5 | 0.46 |
| | 3 | III | 12 | [B(14-21)]---[A(18-21)] | ALYLVCGE---NYCG | SEQ ID NO: 6 | 0.76 |
| | 4 | IV | 26 | [B(1-13)]---[A(5-17)] | FVNQHLCGSHLVE---QCCTSICSLYQLE | SEQ ID NO: 4 | 1 |
| Insulin Aspart | 1 | I | 4 | [A(1-4)] | GIVE | SEQ ID NO: 1 | 0.37 |
| | 2 | II | 9 | [B(22-30)] | RGFFYTDKT | SEQ ID NO: 15 | 0.56 |
| | 3 | III | 12 | [B(14-21)]---[A(18-21)] | ALYLVCGE---NYCG | SEQ ID NO: 6 | 0.73 |
| | 4 | IV | 26 | [B(1-13)]---[A(5-17)] | FVNQHLCGSHLVE---QCCTSICSLYQLE | SEQ ID NO: 4 | 1 |
| Insulin Lispro | 1 | I | 4 | [A(1-4)] | GIVE | SEQ ID NO: 1 | 0.4 |
| | 2 | II | 9 | [B(22-30)] | RGFFYTKPT | SEQ ID NO: 7 | 0.59 |
| | 3 | III | 12 | [B(14-21)]---[A(18-21)] | ALYLVCGE---NYCN | SEQ ID NO: 3 | 0.74 |
| | 4 | IV | 26 | [B(1-13)]---[A(5-17)] | FVNQHLCGSHLVE---QCCTSICSLYQLE | SEQ ID NO: 4 | 1 |

Fragment IV contained amino acids A5-A17 and B1-B13, Fragment III A18-A21 and B14-B21, Fragment II B22-B30, and Fragment I A1-A4. These 4 peptide fragments eluted sequentially with the smaller peptide fragments eluting more rapidly. Fragment I of 4 amino acids eluted first in $10^{th}$ min and showed the lowest UV absorbance. Fragment II of 9 amino acids eluted at about $16^{th}$ min followed by Fragment III, which contained 12 amino acids, eluted from the column about 2.7 mins later than Fragment II. Fragment IV containing 26 amino acids eluted at about $26^{th}$ min and showed the highest level of UV absorption.

Fragment I and IV eluted at about same retention time for the rest of the analogues (Aspart, Glargine & Lispro) as there is no change in sequence (with respect to number of amino acids) when compared to insulin. Fragment II for Aspart & Lispro (despite of change in sequence: Aspart—ProB28 replaced by AspB28; Lispro—LysB29→ProB29 switch) eluted at the same retention time as of insulin. Fragment III for Aspart & Lispro eluted at the same retention time as of insulin as there is no change in sequence (with respect to number of amino acids). Insulin Glargine showed a significant shift in the retention times of fragments II and III as compared with those of insulin human. Substitution of AsnA21 with Gly on insulin glargine delayed the retention time of Fragment III. Moreover, addition of 2 arginines on Fragment II of insulin glargine (ArgB31-32) brought the elution ahead of that of insulin human.

Figure 2:
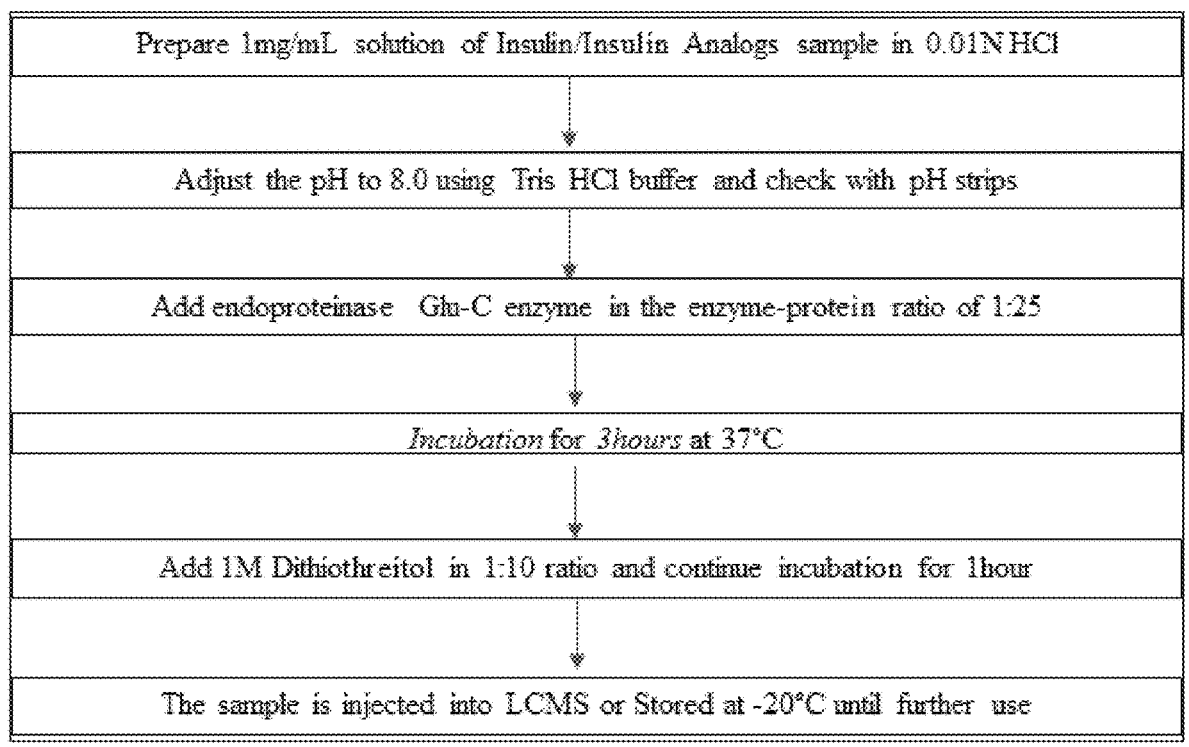
FIG. 2 represents flowchart of enzymatic digestion under reduced condition of working standards (in-house) and commercial products.
Figure 3:
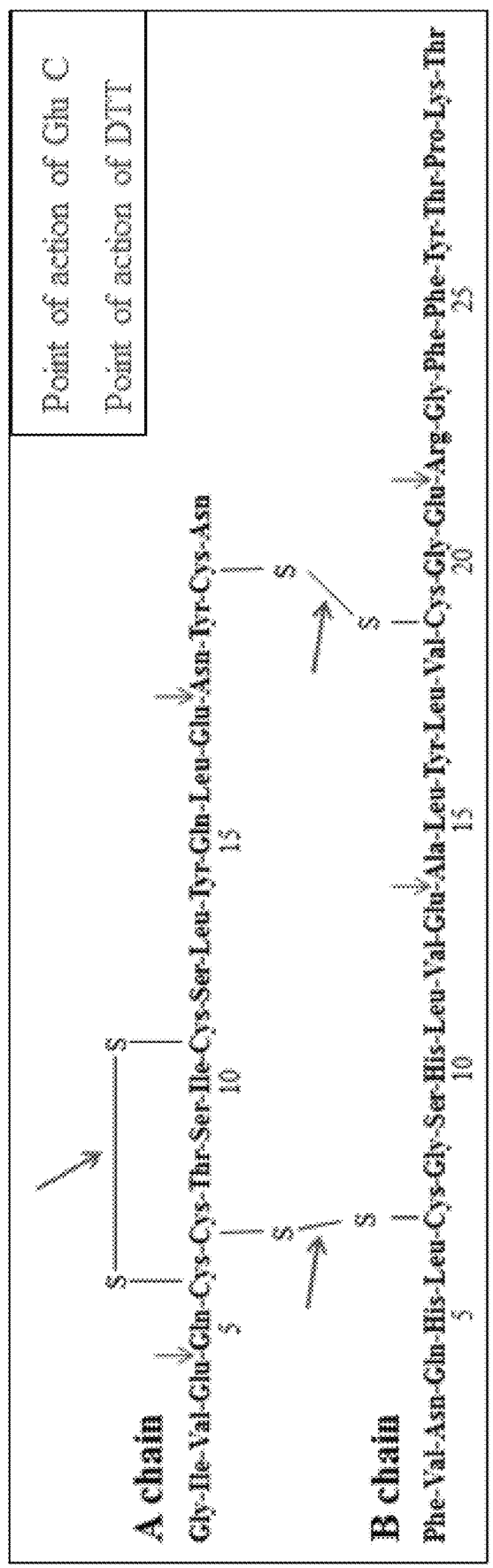
FIG. 3 represents points of action of endonuclease Glu-C and DTT on human insulin.
Figure 4:
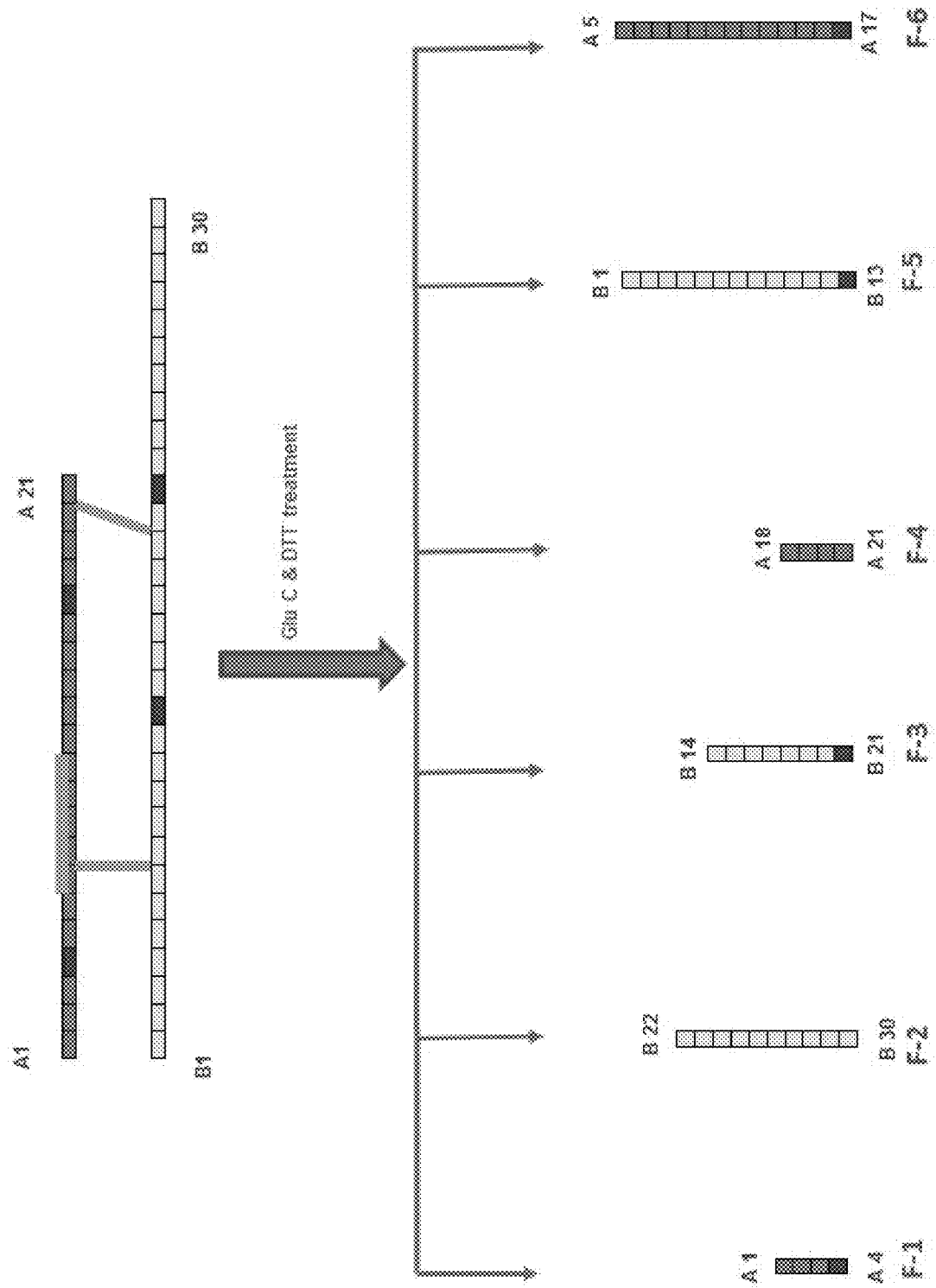
FIG. 4 represents Insulin—Peptide fragments after Digestion and Reduction.

Step 2 Enzymatic Digestion with Reduction of In-House Working Standards and Commercial Products Step by step procedure was followed as displayed in FIG. 2, wherein, the protein sample (1 mg/mL) was dissolved in 0.01 N HCl and the pH is adjusted to 7.5-8.5 with Tris-HCl buffer. Endoproteinase Glu-C was added in the ratio 25:1 (protein to enzyme). The sample was incubated at 37° C. for 3 hours. The step for reduction would be adding 1 M DTT and continue incubating at 37° C. for 1 hour. Then the final sample was analysed using a LC-MS (ESI) for the HPLC and Protein mass fingerprinting (PMF) profiles. The sample was also stored at −20° C. for future use. FIGS. 3 and 4 depict the point of action upon of Glu-C and DTT, and fragments generated, when protein sample of Insulin or insulin analogue is digested under reduced condition.

Six peptide fragments were generated from human Insulin Molecule after Glu-C Digestion under reducing condition. Fragment I of 4 amino acids eluted first in 5.2th min; Fragment II of 4 amino acids eluted at about 9.7th min, which showed the lowest UV absorbance followed by Fragment III, which contained 13 amino acids, eluted from the column about 5.0 mins later than Fragment II. Fragment IV containing 9 amino acids eluted at about 15.5th min; Fragment V of 8 amino acids eluted at about 23.8th min and finally Fragment VI of 13 amino acids eluted at about 28.5th min.

TABLE 2

Tabulation of the theoretical masses for Peptide fragments of Insulin obtained after Glu-C Digestion under reducing condition

| Analog | Sr. No | Frag. No | No of AA | Position of Sequence | Sequence | | RRT |
|---|---|---|---|---|---|---|---|
| Human Insulin | 1 | I | 4 | [A(18-21)] | NYCN | SEQ ID NO: 8 | 0.18 |
| | 2 | II | 4 | [A(1-4)] | GIVE | SEQ ID NO: 1 | 0.33 |
| | 3 | III | 9 | [B(22-30)] | RGFFYTPKT | SEQ ID NO: 2 | 0.52 |
| | 4 | IV | 13 | [B(1-13)] | FVNQHLCGSHLVE | SEQ ID NO: 9 | 0.54 |
| | 5 | V | 8 | [B(14-21)] | ALYLVCGE | SEQ ID NO: 10 | 0.85 |
| | 6 | VI | 13 | [A(5-17)] | QCCTSICSLYQLE | SEQ ID NO: 11 | 1 |
| Insulin Glargine | 1 | I | 4 | [A(18-21)] | NYCG | SEQ ID NO: 12 | 0.21 |
| | 2 | II | 4 | [A(1-4)] | GIVE | SEQ ID NO: 1 | 0.34 |
| | 3 | III | 11 | [B(22-32)] | RGFFYTPKTRR | SEQ ID NO: 13 | 0.4 |
| | 4 | IV | 12 | [B(1-13)] | FNQHLCGSHLVE | SEQ ID NO: 14 | 0.52 |
| | 5 | V | 8 | [B(14-21)] | ALYLVCGE | SEQ ID NO: 10 | 0.83 |
| | 6 | VI | 13 | [A(5-17)] | QCCTSICSLYQLE | SEQ ID NO: 11 | 1 |
| Insulin Aspart | 1 | I | 4 | [A(18-21)] | NYCN | SEQ ID NO: 8 | 0.18 |
| | 2 | II | 4 | [A(1-4)] | GIVE | SEQ ID NO: 1 | 0.34 |
| | 3 | III | 9 | [B(22-30)] | RGFFYTDKT | SEQ ID NO: 15 | 0.53 |
| | 4 | IV | 13 | [B(1-13)] | FVNQHLCGSHLVE | SEQ ID NO: 9 | 0.55 |
| | 5 | V | 8 | [B(14-21)] | ALYLVCGE | SEQ ID NO: 10 | 0.9 |
| | 6 | VI | 13 | [A(5-17)] | QCCTSICSLYQLE | SEQ ID NO: 11 | 1 |
| Insulin Lispro | 1 | I | 4 | [A(18-21)] | NYCN | SEQ ID NO: 8 | 0.19 |
| | 2 | II | 4 | [A(1-4)] | GIVE | SEQ ID NO: 1 | 0.33 |
| | 3 | III | 9 | [B(22-30)] | RGFFYTKPT | SEQ ID NO: 7 | 0.5 |
| | 4 | IV | 13 | [B(1-13)] | FVNQHLCGSHLVE | SEQ ID NO: 9 | 0.51 |
| | 5 | V | 8 | [B(14-21)] | ALYLVCGE | SEQ ID NO: 10 | 0.77 |
| | 6 | VI | 13 | [A(5-17)] | QCCTSICSLYQLE | SEQ ID NO: 11 | 1 |

In insulin Lispro, there was no change in elution patterns for fragments except for fragment IV where it significantly eluted at 14.4th min which was around 1 min ahead of the human insulin fragment IV elution.

Insulin Glargine, there was no change in elution patterns for fragments II, III, V and VI as there was no change in sequence. Fragment I eluted at 5.8th min as there was change in sequence (substitution of AsnA21 with Gly). Fragment IV eluted ahead at 11.4th min, when compared to Human Insulin and Insulin Lispro because of the change in sequence which is addition of 2 arginines (ArgB31-32).

Insulin Aspart, peptide mass fingerprinting was carried out using 80% ACN as eluent B. Fragment I of 4 amino acids eluted first in 5.3th min; Fragment II of 4 amino acids eluted at about 10.4th min, which showed the lowest UV absorbance followed by Fragment III, which contained 13 amino acids, eluted from the column about 5.5 mins later than Fragment II. Fragment IV containing 9 amino acids eluted at about 16.2th min; Fragment V of 8 amino acids eluted at about 26.9th min and finally Fragment VI of 13 amino acids eluted at about 30.5th min.

Step 3: Reverse-Phase High Performance Liquid Chromatography (RP-HPLC)

The RP-HPLC was performed on Agilent 1200 HPLC system with a Diode Array Detector (USA) connected to Mass Spectrometer (Bruker HCT). A gradient system was employed with a flow rate of 1.0 mL/min.

As shown in table 3 the mobile phase included 100% water with 0.1% FA as eluent A and 90% acetonitrile as eluent B [for insulin and insulin analogues (digestion) & for Insulin, Glargine, Lispro (digestion & Reduction)]. In case of Aspart (digestion & reduction), 80% ACN was used as eluent B.

TABLE 3

Reverse-Phase High Performance Liquid Chromatography (RP-HPLC) conditions

| | Digestion | | | Digestion + Reduction | | |
|---|---|---|---|---|---|---|
| | Mobile Phase | Eluent A | Eluent B | Mobile Phase | Eluent A | Eluent B |
| Insulin | 100% Water | 0.1% Formic Acid | 90% Acetonitrile | 100% Water | 0.1% Formic Acid | 90% Acetonitrile |
| Insulin Lispro | 100% Water | 0.1% Formic Acid | 100% Acetonitrile | 100% Water | 0.1% Formic Acid | 100% Acetonitrile |
| Insulin Glargine | 100% Water | 0.1% Formic Acid | 90% Acetonitrile | 100% Water | 0.1% Formic Acid | 90% Acetonitrile |
| Insulin Aspart | 100% Water | 0.1% Formic Acid | 90% Acetonitrile | 100% Water | 0.1% Formic Acid | 80% Acetonitrile |

TABLE 4

Reverse-Phase High Performance Liquid Chromatography (RP-HPLC) conditions

| Time | Eluent B |
|---|---|
| Initial Condition | 5% |
| 0 to 12 mins | 5-20% |
| 12 to 18 mins | 20-21% |
| 18 to 25 mins | 21-30% |
| 25 to 34 mins | 30-70% |
| 34 to 34.10 mins | 70-5% |
| 34.10 to 40 mins | 5% (Wash) |

The initial condition was 5% eluent B and then 5-20% eluent B from 0 to 12 mins, 20-21% eluent B from 12 to 18 mins, 21-30% eluent B from 18 to 25 mins, and 30-70% eluent B from 25 to 34 mins and 70-5% eluent B from 34 to 34.10 mins and left for further 6.0 mins to re-equilibrate (Table 4).

5 microliters digested sample solutions were injected and analysed on ACE C18-300 column (4.6×250 mm, 5 μm particle size; Aberdeen, Scotland) maintained at a column temperature of 40° C. Fractionated insulin and insulin analogue peptides were detected by UV absorbance at 220 nm.

Step 4: Mass Spectrometry

Bruker High Capacity Trap was used for mass spectrometry analysis with following parameters for the analysis reference;
1. Ion source type—ESI Positive,
2. Mass Range Mode—Ultra Scan,
3. Ion Polarity—Positive,
4. Scan Range—50-2200 m/z, Auto $MS^n$-On.

Peptide mass fingerprinting was performed for protocols of Step 1 and Step 2.

HPLC chromatograms for digestion and digestion and reduction were examined for all the samples analysed. Additionally, mass spectrometry data was also obtained for confirmation of the masses for the peaks attained. Peptide mapping technique was able to distinguish between human insulin and various types of insulin analogues more effectively than liquid chromatography ensured and displayed a capability to reveal elusive differences.

The following examples serve to illustrate certain preferred embodiments and aspects of the present invention and are not to be construed as limiting the scope thereof.

Example 1: Digestion of Insulin Molecule

Four peptide fragments were generated from insulin human after protease V8 digestion Fragment IV contained amino acids A5-A17 and B1-B13, Fragment III A18-A21 and B14-B21, Fragment II B22-B30, and Fragment IV A1-A4. These 4 peptide fragments eluted sequentially with the smaller peptide fragments eluting more rapidly. Fragment I of 4 amino acids eluted first in 10th min and showed the lowest UV absorbance. Fragment II of 9 amino acids eluted at about 16th min followed by Fragment III, which contained 12 amino acids, eluted from the column about 2.7 mins later than Fragment II. Fragment IV containing 26 amino acids eluted at about 26th min and showed the highest level of UV absorption.

Figure 5:
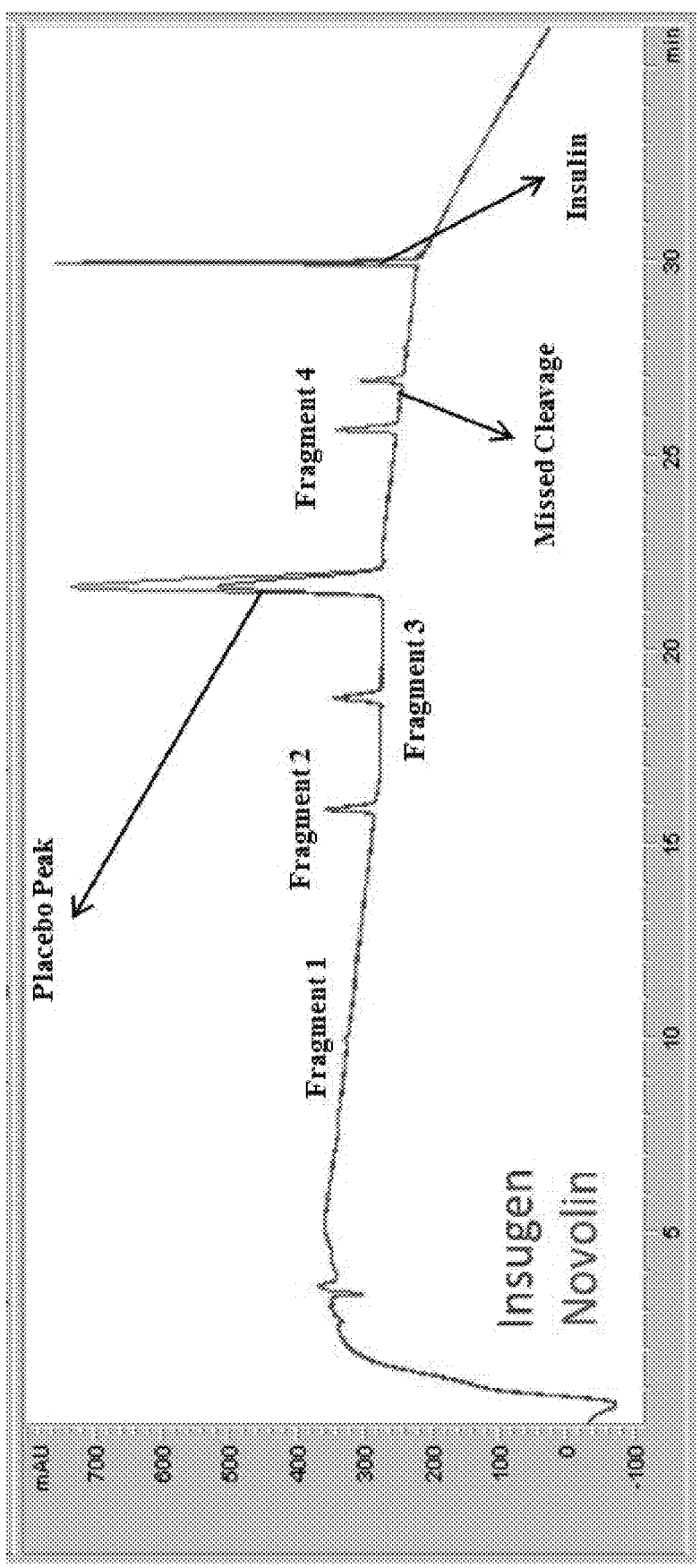
FIG. 5 represents overlays of Insulin samples under digestion conditions
Figure 7:
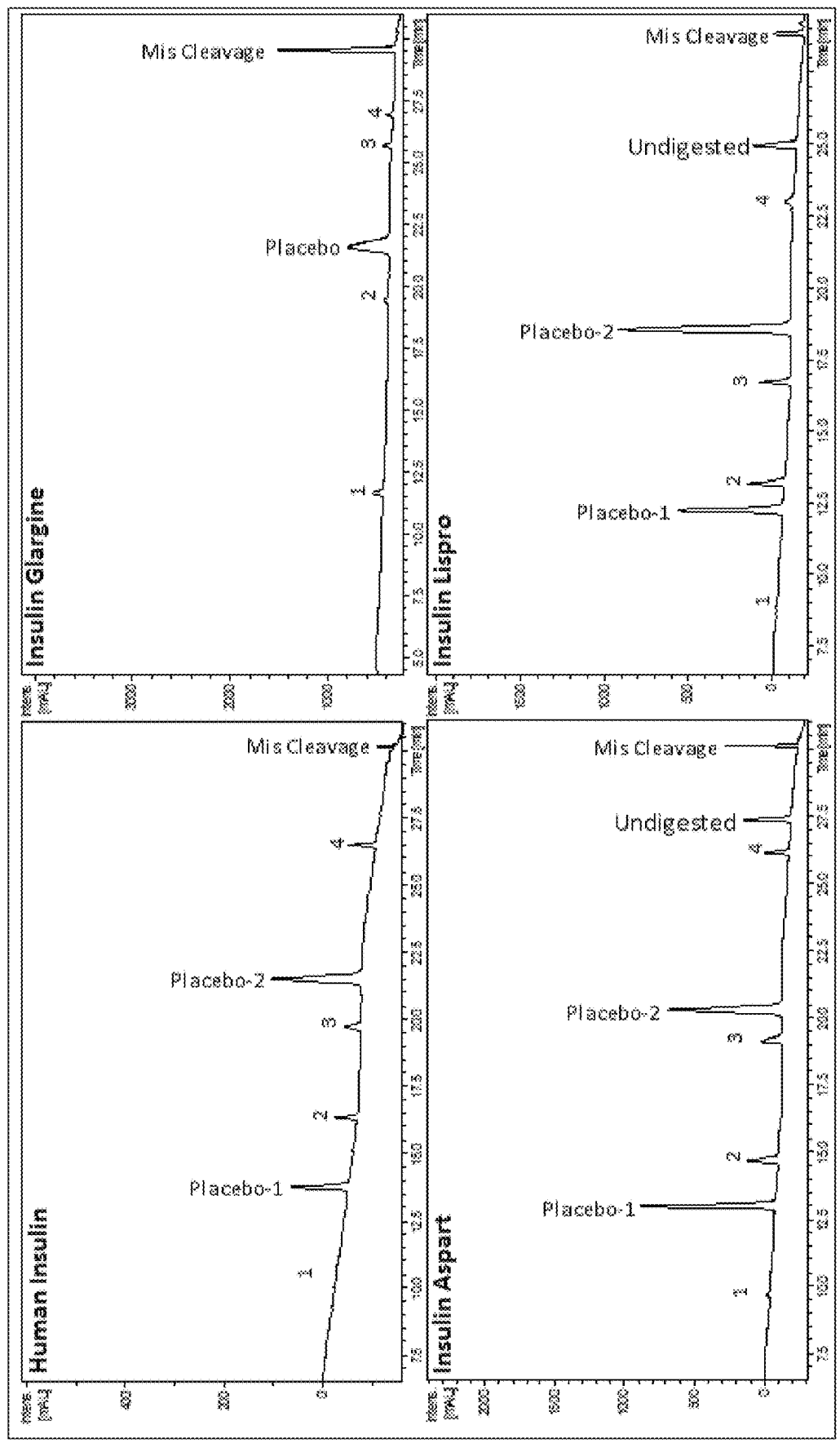
FIG. 7 represents digestion profiles of Human Insulin, Insulin Glargine, Insulin Aspart and Insulin Lispro.
Figure 9:
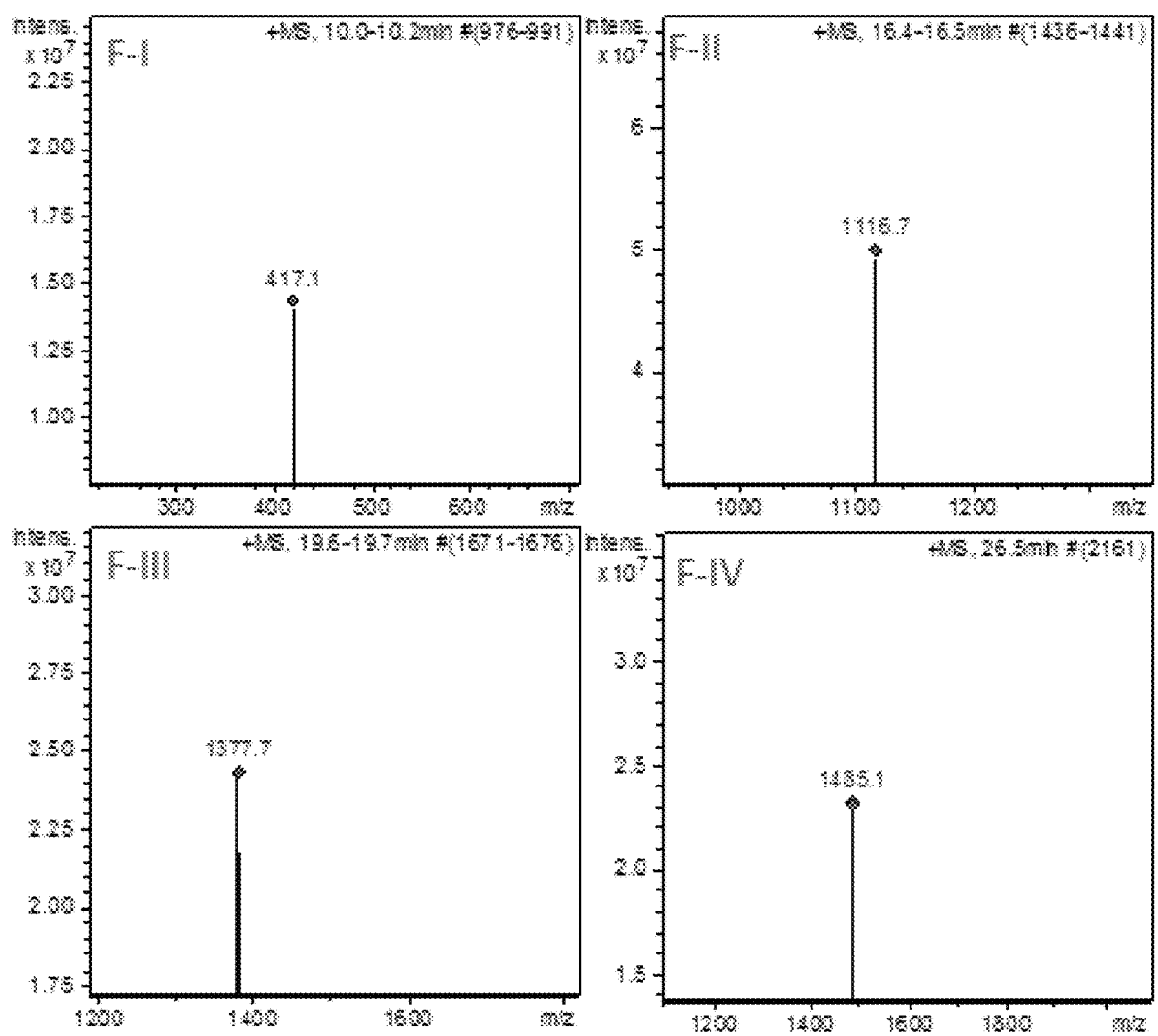
FIG. 9 represents four fragments of Human Insulin after digestion which confirms the masses of fragments.

FIG. 5 represents the overlays of Insulin samples (In-house product Insugen and commercial product Novolin) under digestion conditions. FIG. 7 shows the fragments generated by the process of digestion as a UV chromatogram whereas FIG. 9 confirms the masses of fragments.

Example 2: Digestion of Insulin Aspart

Four peptide fragments were generated from insulin human after protease V8 digestion Fragment IV contained amino acids A5-A17 and B1-B13, Fragment III A18-A21 and B14-B21, Fragment II B22-B30, and Fragment IV A1-A4. Fragment I and IV eluted at about same retention time as of Insulin molecule as there is no change in sequence when compared to insulin. Fragment II for Aspart (despite of change in sequence: Aspart—ProB28 replaced by AspB28 switch) eluted at the same retention time as of insulin. Fragment III for Aspart eluted at the same retention time as of insulin as there is no change in sequence.

Figure 11:
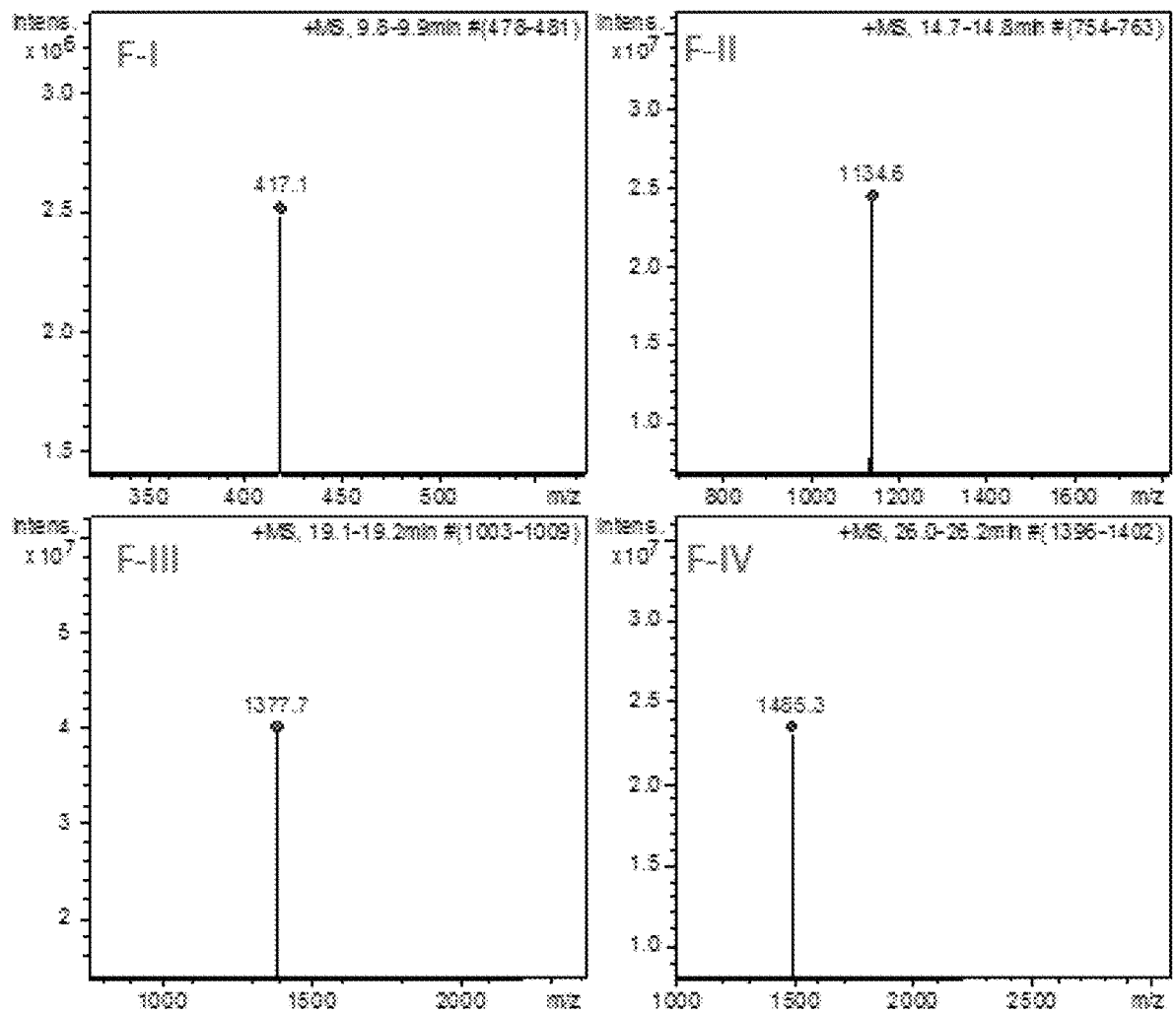
FIG. 11 represents four fragments of Insulin Aspart after digestion confirms the masses of fragments.

FIG. 7 represents the fragments generated by the process of digestion as a UV chromatogram wherein FIG. 11 confirms the masses of fragments.

Example 3: Digestion of Insulin Lispro

Four peptide fragments were generated from insulin human after protease V8 digestion Fragment IV contained amino acids A5-A17 and B1-B13, Fragment III A18-A21 and B14-B21, Fragment II B22-B30, and Fragment IV A1-A4. Fragment I and IV eluted at about same retention time as of Insulin molecule as there is no change in sequence when compared to insulin. Fragment II for Lispro (despite of change in sequence: Lispro—LysB29→ProB29 switch) eluted at the same retention time as of insulin. Fragment III for Lispro eluted at the same retention time as of insulin as there is no change in sequence.

Figure 12:
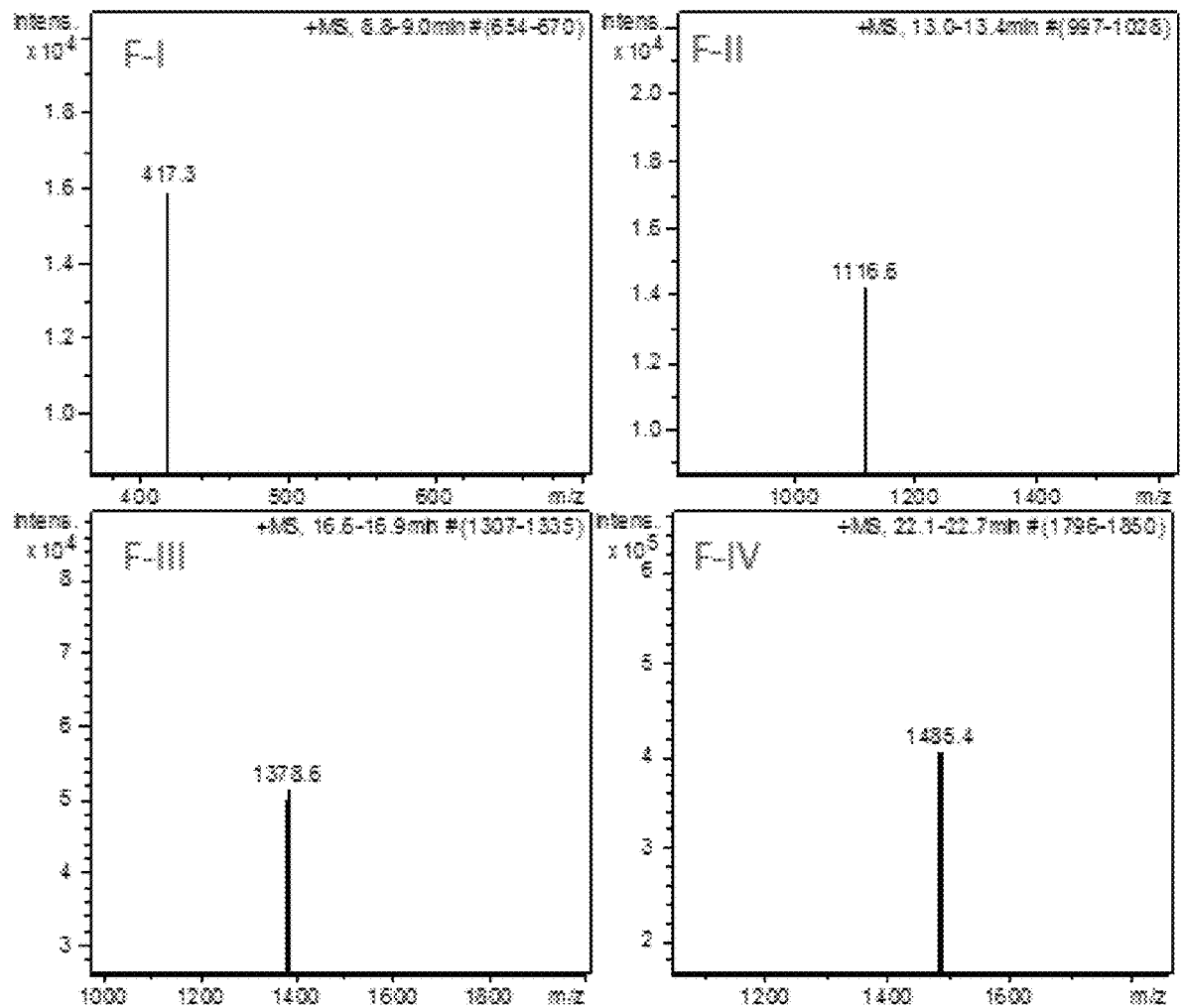
FIG. 12 represents four fragments of Insulin Lispro after digestion confirms the masses of fragments.

FIG. 7 represents the fragments generated by the process of digestion as a UV chromatogram while FIG. 12 confirms the masses of fragments.

Example 4: Digestion of Insulin Glargine

Figure 10:
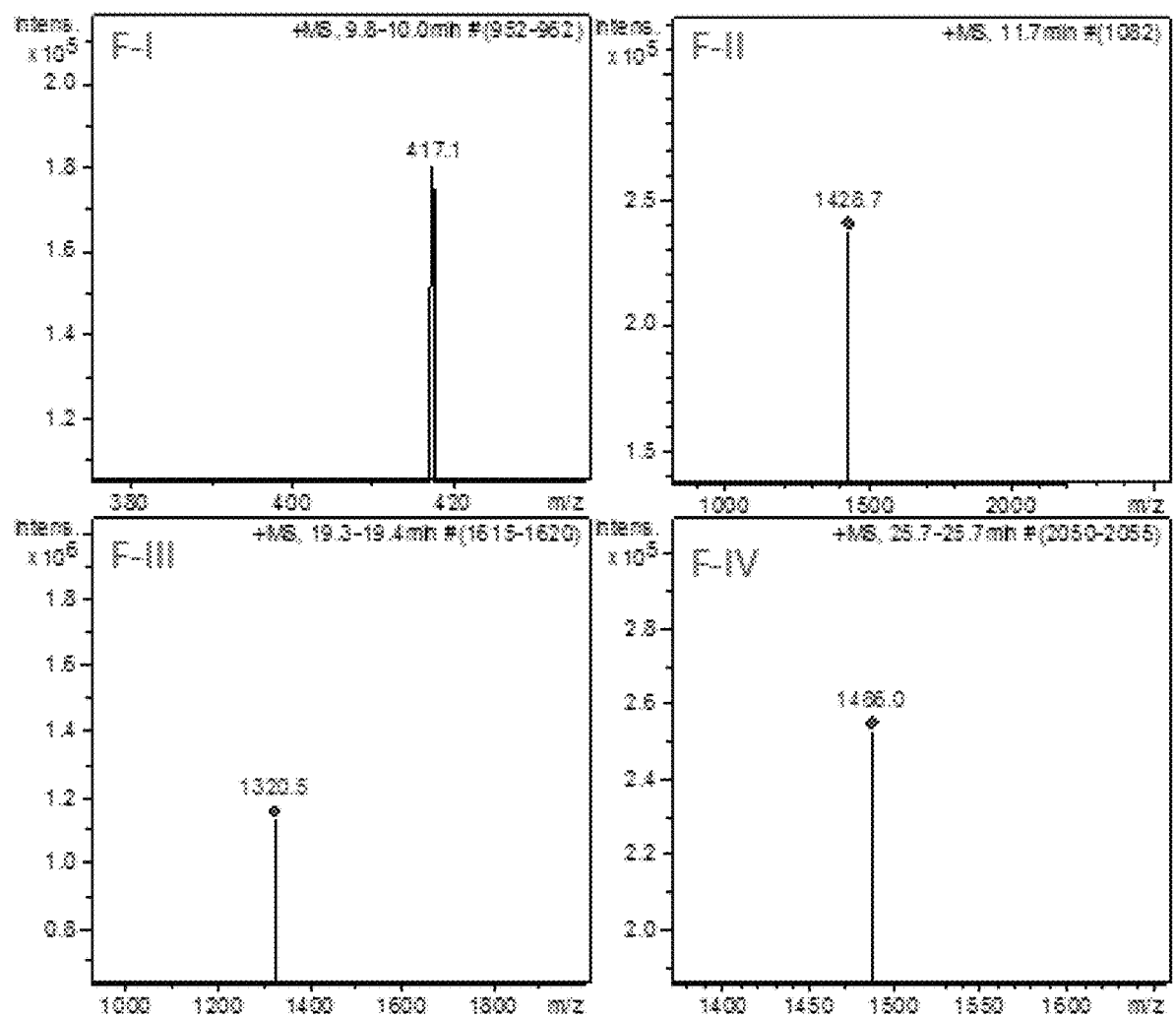
FIG. 10 represents four fragments of Insulin Glargine after digestion confirms the masses of fragments.

Four peptide fragments were generated from insulin human after protease V8 digestion Fragment IV contained amino acids A5-A17 and B1-B13, Fragment III A18-A21 and B14-B21, Fragment II B22-B30, and Fragment IV A1-A4. Insulin Glargine showed a significant shift in the retention times of fragments II and III as compared with those of insulin human. Substitution of AsnA21 with Gly on insulin glargine delayed the retention time of Fragment III. Moreover, addition of 2 arginines on Fragment II of insulin glargine (ArgB31-32) brought the elution ahead of that of insulin human. FIG. 7 shows the fragments generated by the process of digestion as a UV chromatogram whereas FIG. 10 confirms the masses of fragments.

Example 5: Digestion of Insulin Molecule Under Reduced Conditions

Six peptide fragments were generated from human Insulin Molecule after Glu-C Digestion under reducing condition. Fragment I of 4 amino acids eluted first in 5.2th min; Fragment II of 4 amino acids eluted at about 9.7th min, which showed the lowest UV absorbance followed by Fragment III, which contained 13 amino acids, eluted from the column about 5.0 mins later than Fragment II. Fragment IV containing 9 amino acids eluted at about 15.5th min; Fragment V of 8 amino acids eluted at about 23.8th min and finally Fragment VI of 13 amino acids eluted at about 28.5th min.

Figure 6:
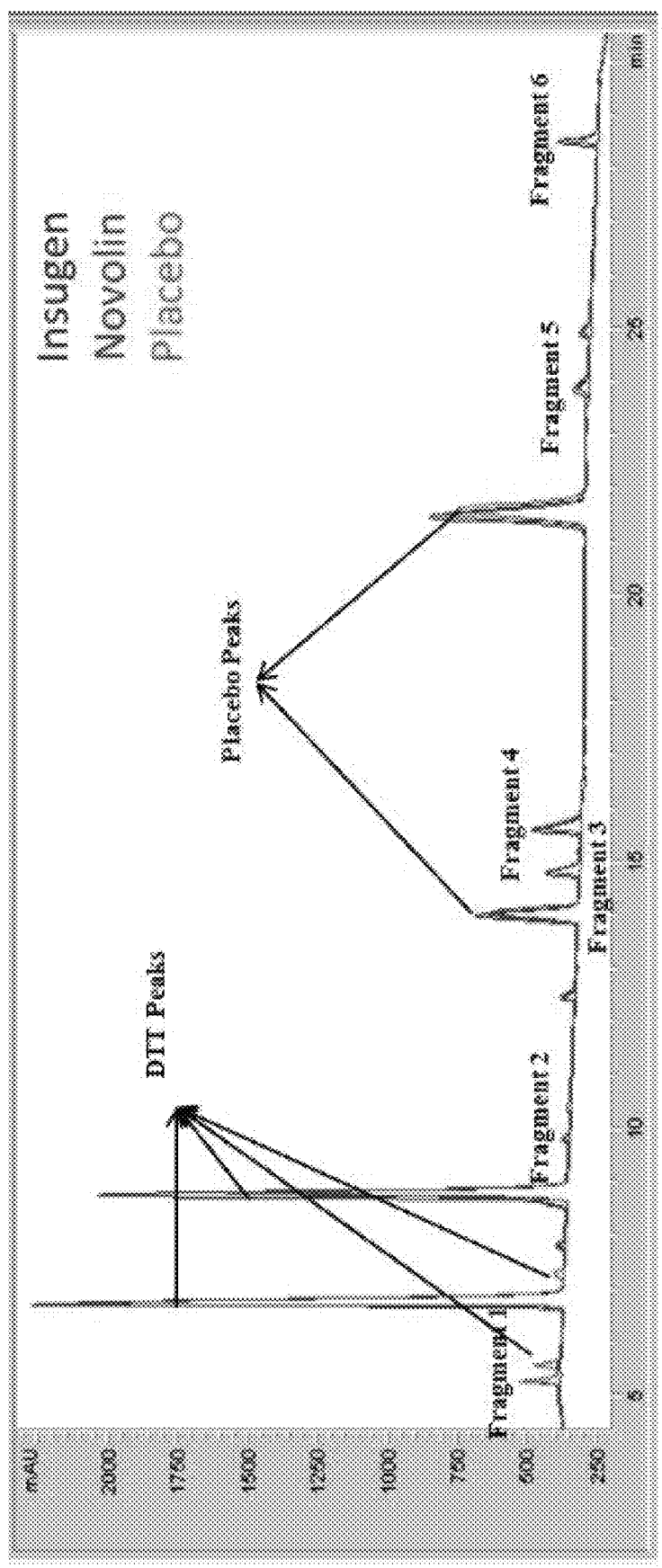
FIG. 6 represents overlays of Insulin samples under digestion and reduced conditions.
Figure 8:
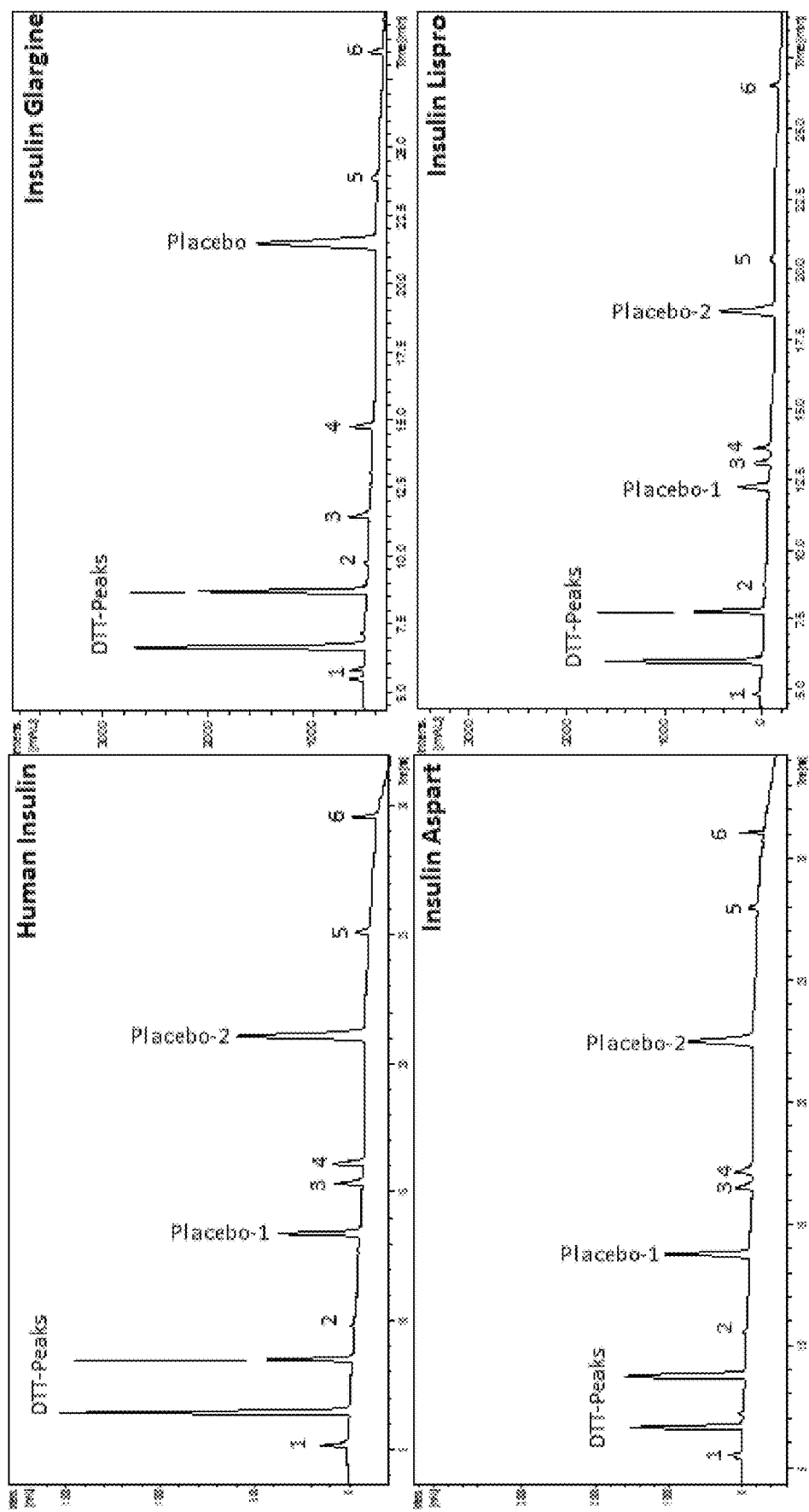
FIG. 8 represents digestion-reduction profiles of Human Insulin, Insulin Glargine, Insulin Aspart and Insulin Lispro.
Figure 13:
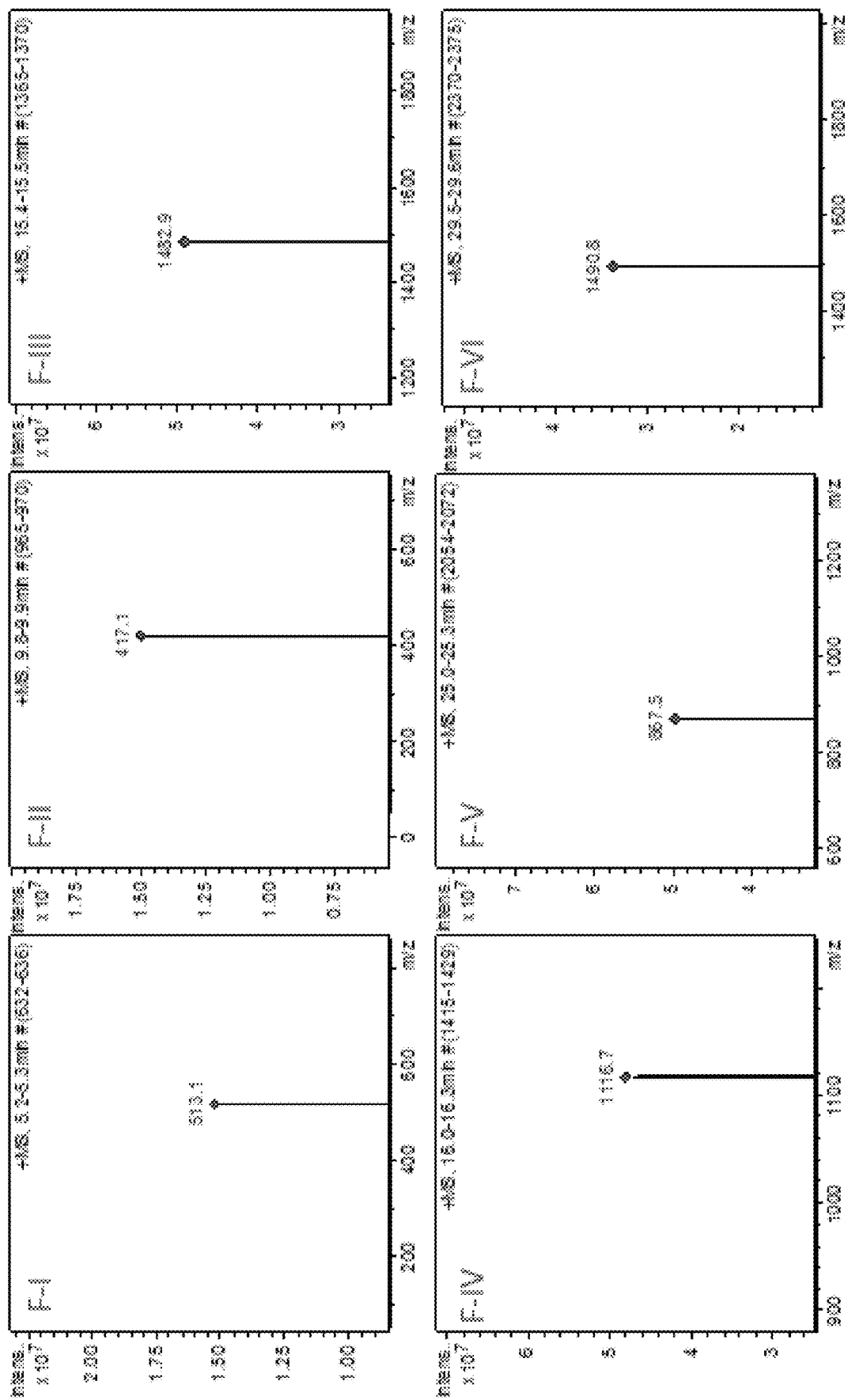
FIG. 13 represents six fragments of Human Insulin after digestion followed by reduction confirms the masses of fragments.

FIG. 6 represents overlays of Insulin samples (In-house product Insugen and commercial product Novolin) under digestion with reduced conditions. FIG. 8 represents the fragments generated by the process of digestion followed by reduction as a UV chromatogram and FIG. 13 confirms the masses of fragments.

Example 6: Digestion of Insulin Aspart Under Reduced Conditions

Figure 15:
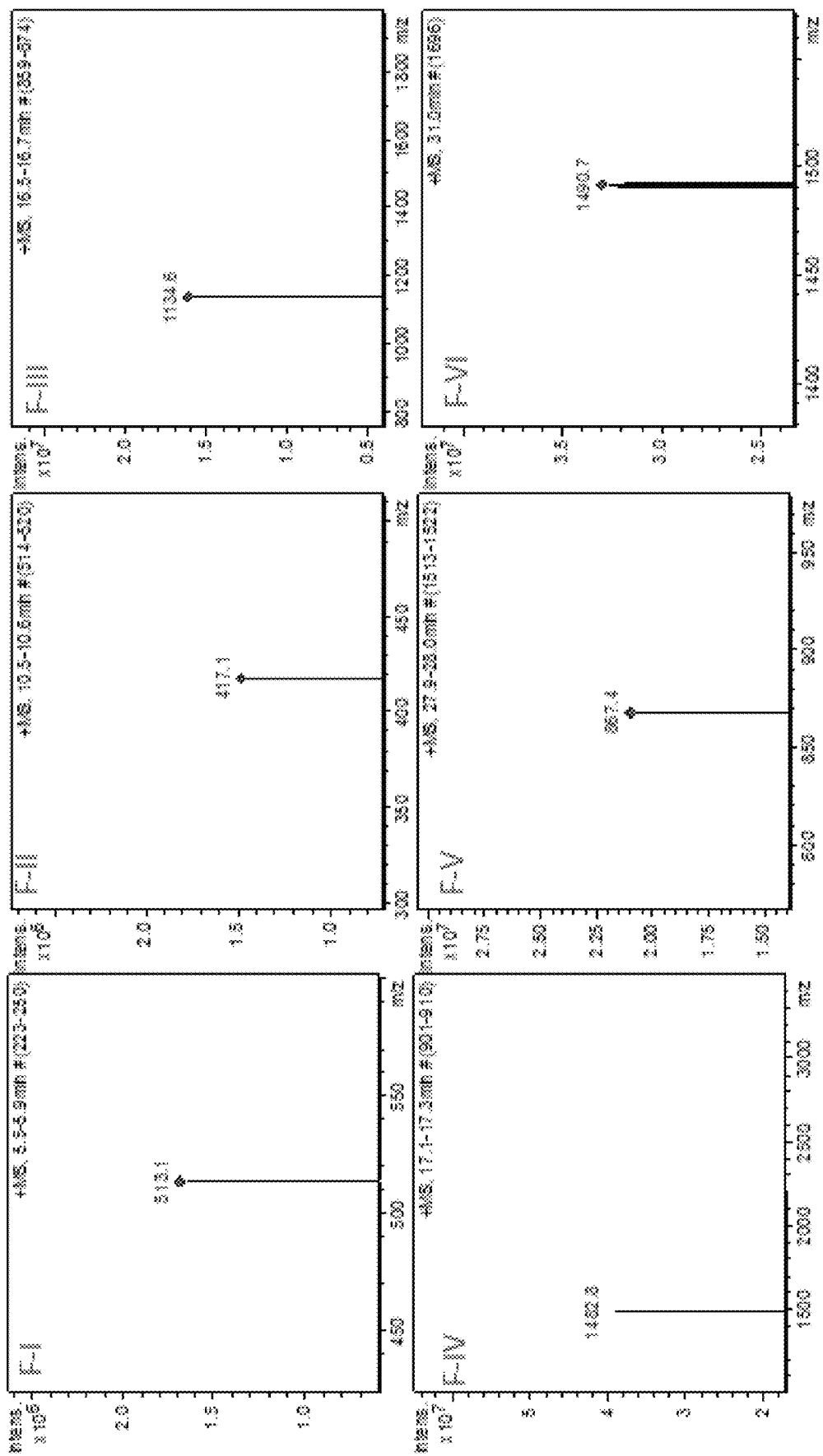
FIG. 15 represents six fragments of Insulin Aspart after digestion followed by reduction confirms the masses of fragments.

Insulin Aspart, peptide mass fingerprinting was carried out using 80% ACN as eluent B. Fragment I of 4 amino acids eluted first in 5.3th min; Fragment II of 4 amino acids eluted at about 10.4th min, which showed the lowest UV absorbance followed by Fragment III, which contained 13 amino acids, eluted from the column about 5.5 mins later than Fragment II. Fragment IV containing 9 amino acids eluted at about 16.2th min; Fragment V of 8 amino acids eluted at about 26.9th min and finally Fragment VI of 13 amino acids eluted at about 30.5th min. FIG. 8 represents the fragments generated by the process of digestion followed by reduction as a UV chromatogram and FIG. 15 confirms the masses of fragments.

Example 7: Digestion of Insulin Lispro Under Reduced Conditions

Figure 16:
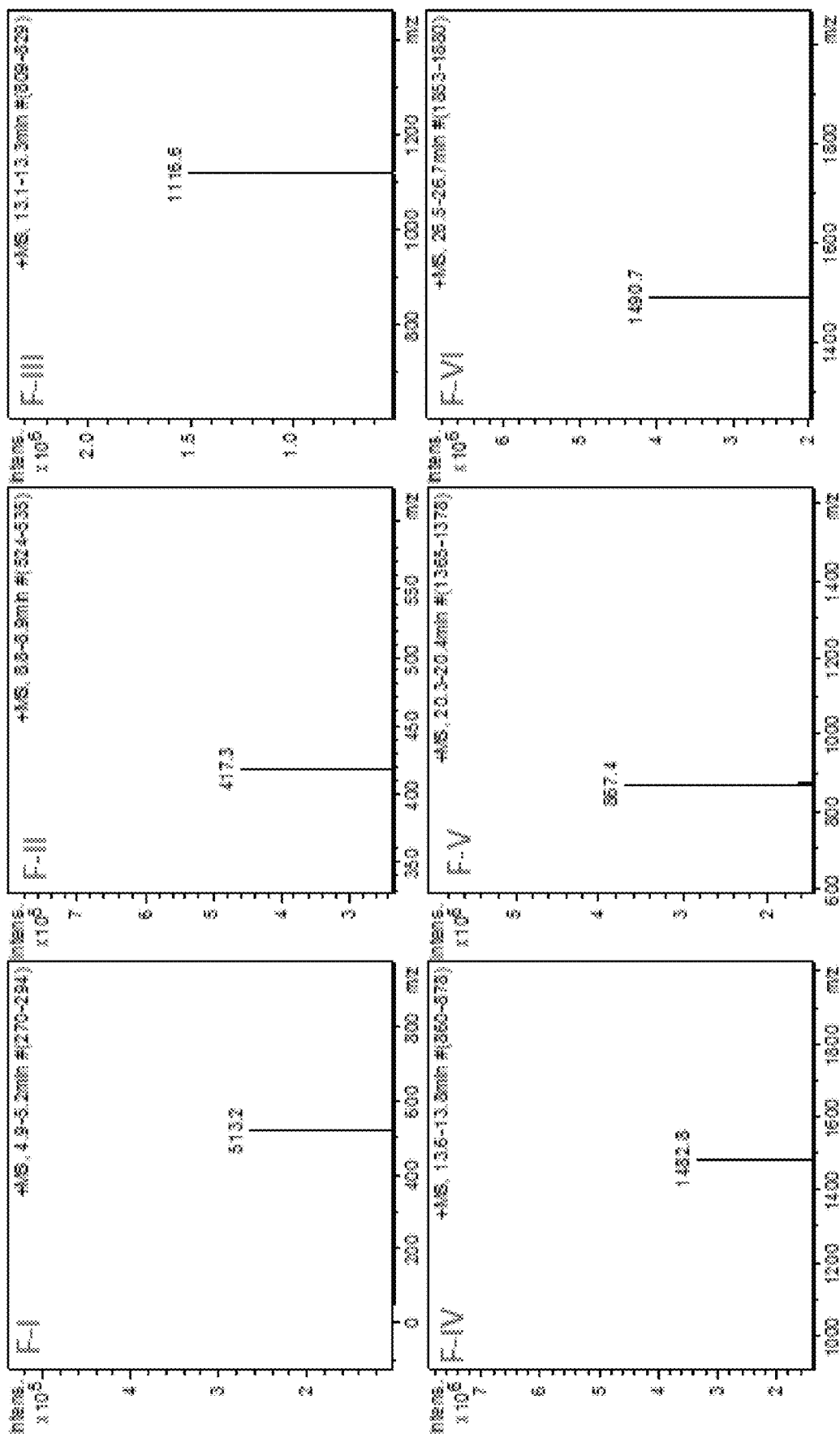
FIG. 16 represents six fragments of Insulin Lispro after digestion followed by reduction confirms the masses of fragments.

Insulin Lispro, there was no change in elution patterns for fragments except for fragment IV where it significantly eluted at 14.4th min which is approx. one min ahead of the human insulin fragment IV elution. FIG. 8 represents the fragments generated by the process of digestion followed by reduction as a UV chromatogram wherein FIG. 16 confirms the masses of fragments.

Example 8: Digestion of Insulin Gargine Under Reduced Conditons

Figure 14:
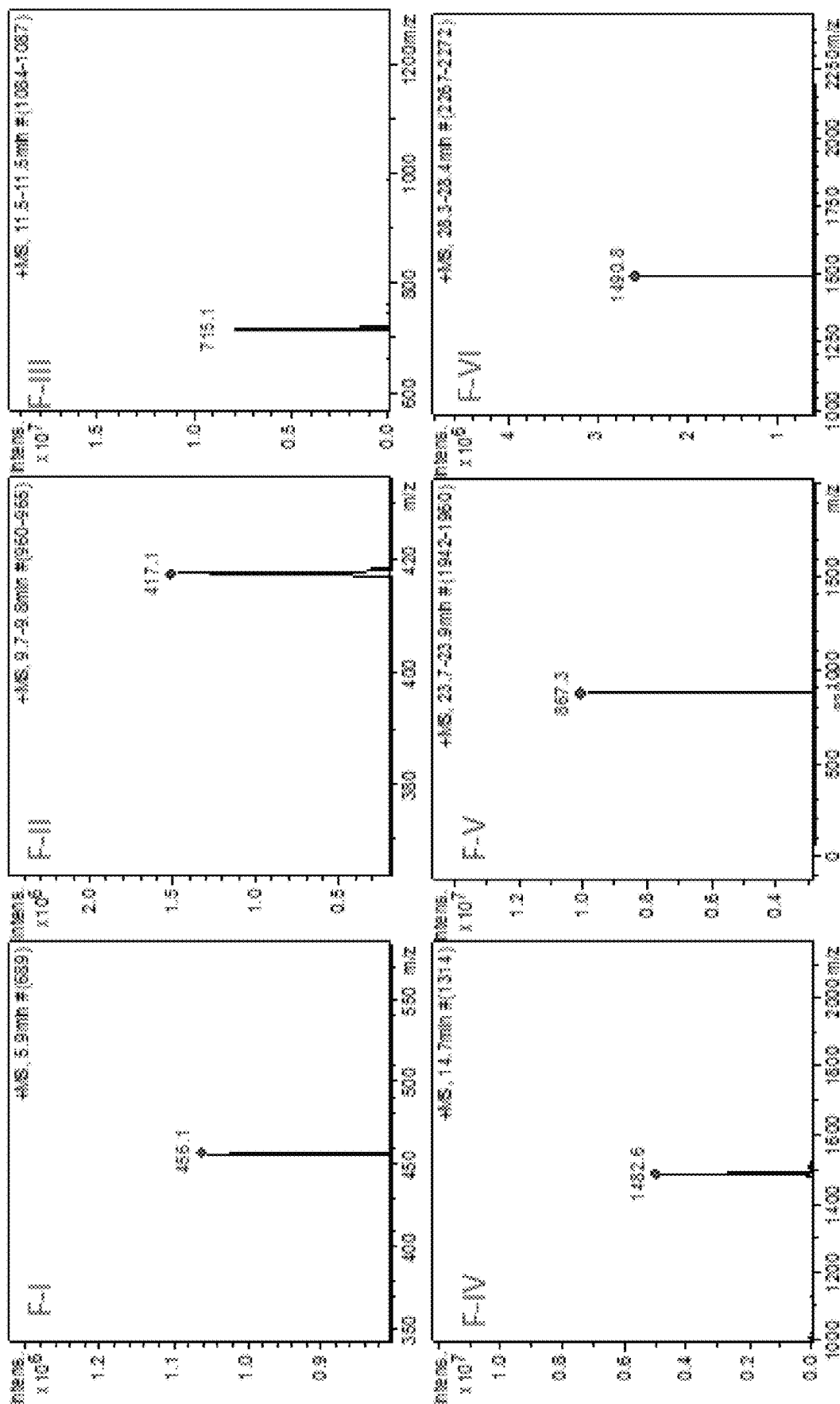
FIG. 14 represents six fragments of Insulin Glargine after digestion followed by reduction confirms the masses of fragments.

Insulin Glargine, there is no change in elution patterns for fragments II, III, V and VI as there is no change in sequence. Fragment I eluted at 5.8th min as there is change in sequence (substitution of AsnA21 with Gly). Fragment IV eluted ahead at 11.4th min, when compared to Human Insulin and Insulin Lispro because of the change in sequence; addition of 2 arginines (ArgB31-32). FIG. 8 represents the fragments generated by the process of digestion followed by reduction as a UV chromatogram. FIG. 14 confirms the masses of six fragments.

Example 9: Comparison of Peptide Maps

Peptide mapping of analysed in-house products tested were identical to the reference products. Moreover, a comparison of the PMF for various insulin analogues with human insulin showed that even a single amino acid change could be detected by peptide mapping. Relating insulin human with insulin lispro, Fragment IV of insulin lispro eluted earlier than that of insulin human suggested that the amino acid rearrangement might induce conformation change and alter the retention time of peptide fragment.

The reducing polarity on Fragment I of insulin glargine caused by substitution of AsnA21 with Gly resulted in delaying retention time. In contrast, additional 2 arginines on Fragment IV increasing the polarity shortened the retention time. Hence we conclude that, the types of insulin analogues could only be effectively identified by PMF, as there was a maximum difference of only 3 amino acids between insulin analogues and human insulin. Chromatograms from FIGS. 7 and 8 represents the comparison of peptide maps from which conclusion was generated.

The mass detection was achieved with both processes, however, the sequence confirmation of polypeptide, wherein there was maximum difference of only 3 amino acids, was achieved by process of digestion followed by reduction of polypeptide.

That which is claimed is:

1. A method for determining the amino acid sequence and mass of a polypeptide or mixture of polypeptide(s), comprising the steps of:
   a) preparing polypeptide sample by dissolving the polypeptide in HCl and adjusting pH by Tris;
   b) digesting the polypeptide sample by addition of endoproteinase Glu C in ratio of 25:1;
   c) reducing the digested sample of step (b) by addition of 1M dithiothreitol;
   d) performing HPLC analysis followed by mass spectrometry analysis of the polypeptide of step (c);
   e) comparing the molecular mass of the polypeptide with the molecular mass of a corresponding known polypeptide, thereby determining the identity of the polypeptide;
   wherein organic solvent used is in step (d) is a non-salt buffer and the method allows sequence confirmation of multiple fragments at the same time.

2. The method as claimed in claim 1, wherein in step (a) the pH is adjusted between 7.5 and 8.5.

3. The method as claimed in claim 1, wherein the non-salt based buffer is selected from a group consisting of acetonitrile, formic acid, TFA, or a combination thereof.

4. The method as claimed in claim 1, wherein the time required for steps (d) and (e) is about 40 minutes.

5. The method as claimed in claim 1, wherein the polypeptide(s) is insulin or insulin analogs.

6. The method as claimed in claim 5, wherein the polypeptide is selected from a group consisting of aspart, lispro and glargine.

7. The method as claimed in claim 1, wherein the polypeptides can differ at least by one amino acid.

8. The method as claimed in claim 1, wherein analyzed fragments of polypeptide(s) of step (e) have a mass ranging from 0.4 kDa to 8 kDa.

* * * * *

SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:

```
<223> OTHER INFORMATION: Synthetic Construct

<400> SEQUENCE: 1

Gly Ile Val Glu
1

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Arg Gly Phe Phe Tyr Thr Pro Lys Thr
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Ala Leu Tyr Leu Val Cys Gly Glu Asn Tyr Cys Asn
1               5                   10

<210> SEQ ID NO 4
<211> LENGTH: 26
<212> TYPE: PRT
<213> ORGANISM: Artificial Sequence
<220> FEATURE:
<223> OTHER INFORMATION: Synthetic construct

<400> SEQUENCE: 4

Phe Val Asn Gln His Leu Cys Gly Ser His Leu Val Glu Gln Cys Cys
1               5                   10                  15

Thr Ser Ile Cys Ser Leu Tyr Gln Leu Glu
            20                  25

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Arg Gly Phe Phe Tyr Thr Pro Lys Thr Arg Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Ala Leu Tyr Leu Val Cys Gly Glu Asn Tyr Cys Gly
1               5                   10

<210> SEQ ID NO 7
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 7

Arg Gly Phe Phe Tyr Thr Lys Pro Thr
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic construct

<400> SEQUENCE: 8

Asn Tyr Cys Asn
1

<210> SEQ ID NO 9
<211> LENGTH: 13
<212> TYPE: PRT
<213> ORGANISM: Artificial Sequence
<220> FEATURE:
<223> OTHER INFORMATION: Synthetic Construct

<400> SEQUENCE: 9

Phe Val Asn Gln His Leu Cys Gly Ser His Leu Val Glu
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Ala Leu Tyr Leu Val Cys Gly Glu
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic Construct

<400> SEQUENCE: 11

Gln Cys Cys Thr Ser Ile Cys Ser Leu Tyr Gln Leu Glu
1               5                   10

<210> SEQ ID NO 12
<211> LENGTH: 4
<212> TYPE: PRT
<213> ORGANISM: Artificial Sequence
<220> FEATURE:
<223> OTHER INFORMATION: Synthetic construct

<400> SEQUENCE: 12

Asn Tyr Cys Gly
1

<210> SEQ ID NO 13
<211> LENGTH: 11
<212> TYPE: PRT
<213> ORGANISM: Artificial Sequence
```

```
<220> FEATURE:
<223> OTHER INFORMATION: Synthetic construct

<400> SEQUENCE: 13

Arg Gly Phe Phe Tyr Thr Pro Lys Thr Arg Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic Construct

<400> SEQUENCE: 14

Phe Asn Gln His Leu Cys Gly Ser His Leu Val Glu
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic construct

<400> SEQUENCE: 15

Arg Gly Phe Phe Tyr Thr Asp Lys Thr
1               5
```